United States Patent [19]

Jensen

[11] Patent Number: 4,967,588
[45] Date of Patent: Nov. 6, 1990

[54] METHOD OF DETERMINING THE AIR BUBBLE SIZE DISTRIBUTION IN FRESH CONCRETE, AN ANALYTICAL ASSEMBLY AND A SAMPLE TAKING DEVICE FOR USE HEREWITH

[75] Inventor: Bent J. Jensen, Hellerup, Denmark

[73] Assignee: Dansk Beton Teknik A/S, Hellerup, Denmark

[21] Appl. No.: 360,130

[22] Filed: Jun. 1, 1989

Related U.S. Application Data

[63] Continuation-in-part of Ser. No. 264,977, Oct. 31, 1988, abandoned.

[30] Foreign Application Priority Data

Nov. 3, 1987 [DK] Denmark .................... 5749/87

[51] Int. Cl.$^5$ ........................... G01N 33/38
[52] U.S. Cl. .................. 73/19.08; 73/61 R
[58] Field of Search .............. 73/19, 23, 61 R

[56] References Cited

U.S. PATENT DOCUMENTS

| | | | |
|---|---|---|---|
| 2,722,825 | 11/1955 | Meyer | 73/19 |
| 2,823,540 | 2/1958 | Patch | 73/19 |
| 2,892,343 | 6/1959 | Chase | 73/19 |
| 4,344,316 | 8/1982 | Nasser | 73/19 |
| 4,866,977 | 9/1989 | Nasser | 73/19 |

FOREIGN PATENT DOCUMENTS

| | | | |
|---|---|---|---|
| 2711666 | 9/1978 | Fed. Rep. of Germany | 73/19 |
| 494688 | 12/1976 | U.S.S.R. | 73/19 |
| 697929 | 11/1979 | U.S.S.R. | 73/19 |

OTHER PUBLICATIONS

Torrans et al., Air Void Systems in Ready-Mixed Concrete Journal of Materials, vol. 5, No. 2, June, 1970.
Menzil; Development and Study of Apparatus and Methods for the Determination of Air in Concrete, Journal of American Concrete, 5-1947.

*Primary Examiner*—Hezron E. Williams
*Attorney, Agent, or Firm*—Fleit, Jacobson, Cohn, Price, Holman & Stern

[57] ABSTRACT

A method for determining the air bubble size distribution in fresh concrete, the air bubble distribution in fresh, or green, concrete being identical to the composition in hardened concrete, and an air bubble system consisting of finely divided bubbles being desirable for the purpose of protecting the concrete against damages caused by frost for example, comprises expelling air bubbles (62) from a sample of fresh concrete (28) by agitation utilizing a magnetic agitator (15), passing the expelled air bubbles (62) released into a bubble preserving sample suspending medium (16), preferably being superposed by another medium (17), registering as a function of time at appropriate intervals the size and amount of air bubbles and determining the air bubble size distribution utilizing the analysis result.

14 Claims, 5 Drawing Sheets

METHOD OF DETERMINING THE AIR BUBBLE SIZE DISTRIBUTION IN FRESH CONCRETE, AN ANALYTICAL ASSEMBLY AND A SAMPLE TAKING DEVICE FOR USE HEREWITH

BACKGROUND OF THE INVENTION

This application is a continuation in part of U.S. application Ser. No. 07/264,977, "A method of determining the quality of an air bubble system in fresh concrete", filed Oct. 31, 1990, now abandoned.

The invention relates to a method of determining the air bubble size distribution or void distribution in fresh mortar, concrete and the like, an analytical assembly and a sample taking device for use herewith.

It is known that an air bubble system amounting to 4-8% in concrete can bring about an enhanced frost resistance in the cast concrete if said system consists of finely divided air bubbles.

The determination of the air content of fresh concrete is commonly used. The object of such methods, however, is usually the determination of the total amount of entrained air in fresh concrete. A method of determining the mean size of the air bubbles in fresh concrete is disclosed in Russian Patent No. 697929, this, however, being a rather incomplete description of the air bubble system.

According to the known art, a complete description of the air bubble or pore size distribution in concrete is only possible using a sample of the cast concrete; in other words: you have to make a laboratory casting and determine the air bubble size distribution, for instance according to ASTM C 457. This method is, however, a very cumbersome method, the pronounced need of a method being based on fresh concrete still prevailing, see for example the program announcement from S.H.R.P. (Strategic Highway Research Program), 4th quarter FY 1988, p. 19-20.

A concrete sample taking device according to the known art comprises a spoon, ladle, trowel, shovel or the like, being used for manually digging up or removing more or less of the concrete to be tested.

SUMMARY OF THE INVENTION

The invention is based on the recognition of the fact that the composition of the air bubble system in fresh concrete before casting is substantially identical to the composition of the system in the cast and hardened concrete.

The invention provides an analytical arrangement for and a method of determining the air bubble size distribution in fresh concrete, mortar or the like, the distribution being a quality parameter, and the method is characterized by the fact that the air bubbles are forced out of a representatively taken sample of the fresh concrete and into a bubble preserving sample suspending medium and subjected to an analysis at a constant temperature in which the expelled air quantity is registered as a function of time and in which the air bubble size is measured, whereupon the air bubble size distribution is determined.

The terms "mortar" and "concrete" as used herein are defined as follows: "concrete" is a mixture of cement, water and sand, for example 0-32 mm, "mortar" is concrete without coarse aggregates, the grain size of the sand being for example 0-6 mm.

The sample suspending medium serves to preserve the structure of the air bubbles, i.e. the size and the number of air bubbles remain unchanged during the expelling from the sample of concrete and the rising into the medium.

By means of this method, establishing the actual pore size distribution, one can predict the quality of a planned casting before it is carried out so that a substandard batch can be rejected while, according to the known art, one must first cast the construction concerned which upon hardening can be sampled and analyzed and only then can one determine if the construction has to be rejected.

By making use of the method concerned it has been shown that a prolonged time of mixing the fresh concrete before the final casting gives rise to a desired high level of small air bubbles and consequently a high specific surface. The same is true of pumping and vibration of the concrete. The method concerned may therefore contribute to quality supervision and concrete production control.

The invention provides a device for taking a sample of fresh mortar from fresh concrete, too, said device comprising a sample container and an adapter being connected with a power drill or the like, for the vibration of the device into a batch of fresh concrete.

BRIEF DESCRIPTION OF THE DRAWINGS

The invention will now be described in detail with reference to the accompanying drawings wherein.

DETAILED DESCRIPTION

In a first aspect of the invention, a method is disclosed, according to which the air bubbles in a sample of fresh concrete are released into a bubble preserving sample suspending medium, the amount of released air being registered as a function of time and the size or number of said air bubbles being measured as a function of time, establishing an empirical relationship, said relationship together with the registration of amount/time being used in the determination of the actual air bubble size distribution in the actual sample. The sample suspending medium comprises at least one of the following media: glycerol, a glycol, an alcohol or solutions thereof in water, alcohol or the like, a solution of at least one salt, a carbohydrate solution or similar media and preferably a suitable dye or coloring agent.

The bubble preserving sample suspending medium may in fact consist of one, two, three or even more different liquids/liquid solutions occurring in different phases, i.e. separated by a difference in density, viscosity or by chemical differences such as hydrophobicity/hydrophilicity.

When operating with a sample suspending medium comprising only one liquid component, said liquid component should preferably be miscible with water. If not miscible with water, the liquid should be of a smaller density than water, because water droplets otherwise will ascend and interfere with the air bubble determination.

When operating with a sample suspending medium comprising more than one liquid component, said medium must comprise at least one (hydrophobic/hydrophilic) liquid or liquid solution having a greater density than that of water.

In principle, the method according to the invention is functions at all temperatures within the limits set by the freezing point and boiling point of the liquid/liquid solution component having the highest and lowest freezing, boiling point respectively. The temperature has to be constant in order to guarantee the reproducibility of the analyzing results.

In a preferred embodiment of the method according to the invention, the sample suspending medium consists of one lower bubble preserving liquid or liquid solution, being superposed by another liquid/liquid solution comprising water, salt solutions, carbohydrate solutions or detergent solutions.

Figure 2:
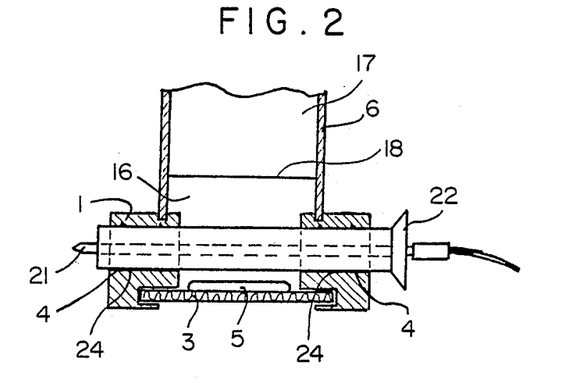
FIG. 2 is a detailed cross-sectional view of the bottom section 1 of the analysis container in FIG. 1, a thermo feeler 21,22 being inserted.

In the following, mainly methods involving two different media are dealt with, these media being referred to as the lower bubble preserving sample suspending medium 16 and the upper medium 17, (see FIG. 2).

In the preferred embodiment the demands are as follows:

The bubble preserving lower medium 16 must have a greater density than the upper medium 17.

In order not to disturb the bubble structure, the lower bubble preserving medium 16 must be compatible with the actual air bubble generating agents.

In order not to negatively influence the establishment of the bubble size/analysis time relationship, later described in detail, the lower bubble preserving medium 16 and the upper medium 17 are not allowed to emulsify or mix under the analyzing conditions.

To achieve a total analysis time of a suitable duration the types and relative amounts of the lower 16 and the upper media 17 must be carefully balanced to achieve a suitable average viscosity, said viscosity being dependent on the temperature employed.

The upper medium 17 must remove the remaining layer of the lower bubble preserving medium 16, if any, on the surface of the air bubbles to ensure a proper determination of the amount of released air bubbles.

The above mentioned demands are for example fulfilled using as the lower bubble preserving sample suspending medium a glycol, an alcohol, glycerol or mixtures thereof with water or alcohol, carbohydrate solutions, salt solutions or mixtures thereof using water or alcohol as the solvent, and using as the superposed upper medium 17 water, solutions in water or alcohol of salt, carbohydrates, detergents or mixtures thereof. The employed temperature depends on the desired time of analysis and on the selected media. A dye or coloring agent is preferably included in the lower bubble preserving sample suspending medium 16, for reasons of convenience, to be sure of the addition of the medium, said addition being otherwise difficult to visualize. Suitable dyes include colored acid-base-indicators, for example methylene blue.

The above mentioned terms are defined as follows:

"glycols" refer to dihydric alcohols, for instance ethylene glycol and propylene glycol; "alcohols" mean compounds of the general formula R-OH wherein R signifies an alkyl group, an aryl group, possibly substituted, for instance ethanole, propanol, cetyl alcohol and cresol; "salt solutions" mean aqueous or alcoholic solutions of at least one salt, for instance sodium chloride, TRIS and sodiumdihydrogenphosphate; "carbohydrate solutions" refer to aqueous or alcoholic solutions of at least one mono-, di- or polysaccharide, for example sucrose, fructose, maltose, glucose, dextran $((C_6H_{10}O_5)_{33}))$ and the like.

The preferred combinations of lower sample suspending bubble preserving medium 16 and upper medium 17 according to the invention are listed in Table 1 below.

TABLE 1

| | List of preferred media (liquids and liquid solutions) according to the invention | | | |
|---|---|---|---|---|
| Upper medium | Lower Sample Susp. Bubble Preserv. Medium | Indicator | Relevant to Cl. No. | Example No. |
| Water | Glycerol | M.B. | 3 | 1 |
| Water | Ethylene glycol | M.B. | 3 | 2 |
| Water | Propylene glycol | M.B. | 3 | 3 |
| Water | Sucrose; 50-70% (w/v) solutions in water | M.B. | 3 | 4 |
| None | 2-Propanol | none | — | — |
| None or water | TRIS; 20-40% (w/v) solutions in water | M.B. | — | — |

In the above table, M.B. designates methylene blue, and water designates demineralized water or tap-water, minor amounts of salts, detergents or carbohydrates being possibly added.

In another preferred embodiment of the method according to the invention, the liberation of the air bubbles from the sample 28 of fresh mortar or concrete results from agitation using a magnetic stirrer 15, the stirrer operating only a short time at the beginning of the analyzing procedure.

The air bubbles might be liberated or released in many other ways, for instance using an impeller, stirrer or agitator of another type, using a vibrational technique, a shaking procedure or centrifuging. The liberating or stirring velocity must be carefully adjusted to the media being actually employed.

In a further embodiment of the invention, the amount of released air bubbles is continuously registered as a function of time by measuring the increase of the buoyancy of an immersed collection bell jar 8 or another upside-down container being immersed in the uppermost medium 17. Said bell jar or container is connected with a weighing unit or scale 14 through a cord or wire mechanism 9,10,12,13, said weighing unit 14 continuously registrating the buoyancy of the bell jar 8, and said buoyancy being equivalent to the total weight of the released air bubbles. The sensitivity of the weighing unit must be carefully adjusted to the media being actually employed. The amount of released air bubbles might of course be registered in many other ways, for example by measuring the pressure rise in a closed system or filling up the previously air filled cavities in the concrete with a liquid and, registering the amount of liquid being consumed, the consumption being equal to the volume of released air (a volumetric scale reading).

In still another preferred embodiment of the invention, the establishment of the empirical relationship between the size of the released air bubbles and the analysis time for a given analyzing set-up proceeds as follows: The air bubbles are released from the sample at the beginning of the analyzing procedure, ascending the lower bubble preserving sample suspending medium 16 and the upper medium 17, samples of which are being taken at appropriate intervals near the upper surface of the uppermost medium 17. The samples are maintained in a fixed condition, no changes of the air bubble structure occurring, until the termination of the calibration procedure, typically for 0.5 hours, or even longer. Then the samples are examined microscopically, preferably a microphotograph is taken, enabling for example the maximum air bubble diameter to be determined as a function of time, see FIGS. 8 and 9.

In the described sample taking procedure, the samples may advantageously be taken utilizing the one part of a conventional frame for a lantern slide or diapositive (bottom up), a drop of the lower medium preferably being added, the one part afterwards being engaged with its counterpart, confining a small sample layer or volume containing the released air bubbles 62 into the interior of the now tightly sealed diapositive frame. In the same fashion, other sample containers having the ability to fix a thin layer of a sample may be used, for example the combination of a microscopical object glass and a cover glass.

The relationship between air bubble size and time may be established in many other ways. For instance through a direct counting procedure, no samples being taken, said counting procedure resulting in the determination of the number of released air bubbles as a function of time, the number-time-relationship together with the previously mentioned amount-time-measurement enabling the calculation of the size-time-relationship being sought. The counting procedure may be conducted opto-electrically, for instance via the breaking of a light ray or beam, or by a light-switch-principle as in a photo-electric cell.

The establishment of the empirical relationship is in fact a calibration procedure, and it is to be conducted in connection with every change in the analyzing parameters, such as type, amount and concentration of all applied media, the type of concrete, the temperature, the stirring time, etc., etc. Once calibrated, a specific analyzing system functions in the same way with the same relationship of bubble size/time with all samples to be analyzed.

In another aspect of the invention, an analytical assembly for performing the method of the invention is disclosed. This assembly comprises a conventional scale 14 (for example a Sartorius L 2200 P scale, having a precision of +0.01 g) with a scale pan 13, a magnetic agitator 15 (for instance from Janke & Kunkel, type R.E.O., without heating ability) and a container for the suspending of the sample 28 to be analyzed and for the immersion of the collection bell jar 8 into the uppermost medium 17. This collection bell jar 8 is in mechanical connection with the pan 13 of the scale 14, in order to effect a weighing of the released air bubbles being collected in the immersed collection bell jar. A thermo control unit 3,21,22 is further included.

Figure 1:
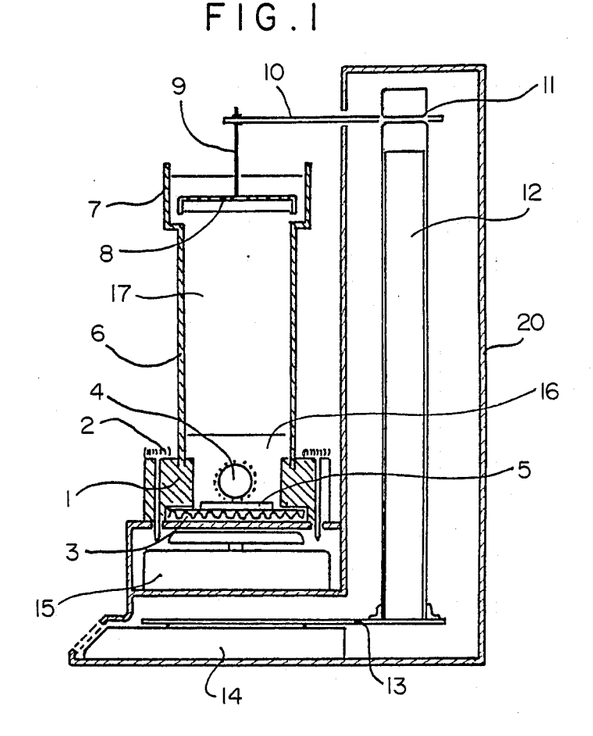
FIG. 1 is a cross-sectional view of an analytical assembly of the invention, comprising an agitator 15, a scale 14 and an analysis container, comprising the sections, 1, 6 and 7.

The container for suspending the sample in the bubble preserving sample suspending medium comprises according to the invention at least two, preferably three, interconnected sections, viz. a bottom section 1, an intermediate section 6 of increased internal cross sectional area or width relative to the bottom section 1, and an upper section 7 of increased internal width relative to the intermediate section 6. The reasons for this gradual enlargement of the container in the direction of ascending of the air bubbles are as follows: the collection bell jar 8, being for example a conventional 9 cm glass Petri dish, must hang down freely, i.e. without coming in touch with the walls of the upper container section 7. Further, in order to collect all the ascending air bubbles, the bell jar 8 (and thus the upper section 7) must have a greater cross sectional area than that of the intermediate section 6 just below. Still further, in order to prevent the air bubbles from settling on the surfaces of the intermediate section 6, this section is of enlarged internal width relative to the bottom section 1, ensuring a minimum distance between the intermediate sectional wall and the nearest ascending air bubbles.

The container sections 1,6,7 can be made of any suitable material, such as stainless steel or other metals or metallic alloys, glass or plastic materials, preferably polymethylmethacrylat (PMMA), in Denmark sold under the trade name Plexiglas (R).

When choosing a transparent material, the immediate supervision of the air bubble releasing and ascending process is possible, although this is not necessarily required.

When providing the bottom section 1 with screws 2 for the securing of the container to the housing or cabinet 20, which is confining the agitator 15, the scale 14 and its mechanical connections 13,12,11 with the collection bell jar 8, the obvious advantage of preventing the container from falling down results, and furthermore slight disturbances, which otherwise might occur, resulting from pushes and bumps, and which might influence the precision of the weighing result, the ascending of the bubbles, etc., are avoided.

Figure 3:
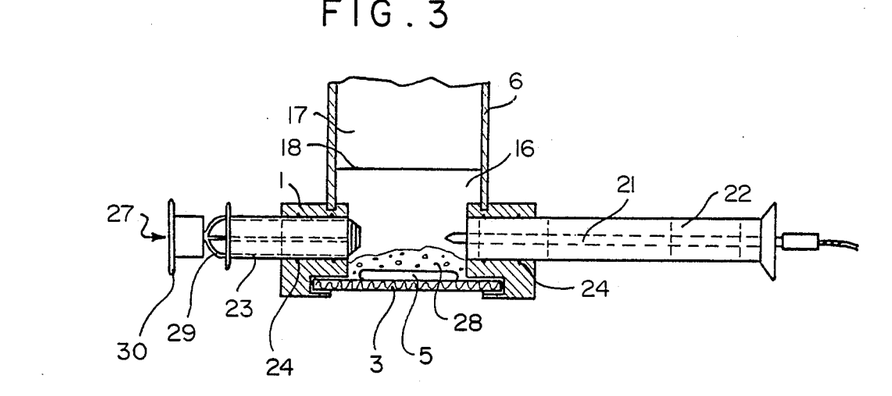
FIG. 3 is a view similar to FIG. 2, the thermo feeler 21,22 being withdrawn and a sample introducing syringe 27 being inserted.

The bottom section 1 is further provided with perforations 4 for the adoption of a sample introducing device 27 and other sensors, if desired, for example a temperature sensor or thermometer 21 for monitoring the temperature of the lower medium 16. Preferably, one throughgoing perforation 4 is made in the bottom section, said perforation being utilized as follows, see FIGS. 2 and 3. Before the analyzing procedure, the thermo feeler 21, being mounted in a suitably sized holder 22, is inserted all way through the perforation 4, thus tightly closing the perforation, in which a number of packing rings 24 are incorporated. Then the liquid media are transferred to the container (FIG. 2) and, just before the starting up of the analyzing procedure, the sample of fresh concrete 28 is introduced into the bottom section 1 of the container by means of a syringe 27, being slowly inserted into the one part of the throughgoing perforation 4, following the withdrawal of the thermo feeler 21 from said one part of the perforation 4, finally leaving the tip of the thermo feeler 21 extending into the lower medium 16, the holder 22 extending rearwardly and tightly sealing the second part of the throughgoing perforation 4, the first part now being tightly closed by the sample introducing syringe 27 (FIG. 3).

The thermo feeler 21 is a tip sensoring instrument, for example an NTC-feeler Testoterm 100 with a measuring range of −50 to +150° C.

The sample introducing syringe 27 is for example a 20 ml Monoject (R) syringe, comprising an outer shield 23, an inner piston 29 and an enlarged grip 30.

The thermo feeler 21 is part of a temperature control system, also comprising an electrical heater 3 in a housing of stainless steel, being mounted in the bottom of the bottom section 1. The controlling of the temperature proceeds via a connected computer.

The container sections 1,6,7 can be variously shaped, the cross sections for example being circular, quadratic or rectangular, although, a circular cross section is preferred. The relative heights of the cylindrical container sections 1,6 and 7 are approximately 1:4:1, respectively, especially 50 mm:200 mm:50 mm, these heights being well suited for performing the method according to the invention within an appropriate time.

The gradual enlargement of the sections 1,6,7 in the direction of the ascending of the air bubbles is preferably obtained by a stepwise increase in the diameter of the sections in a ratio of approximately 5:6:8, especially 70 mm:85 mm:110 mm, these diameters satisfactorily fulfilling the above mentioned requirements, i.e. no settling of air bubbles at the surfaces, the collection bell jar 8 freely hanging down, etc.

The preferred mechanical connection between the collection bell jar 8 and the scale 14, in order to obtain a registration of the weight of the released air bubbles, comprises a rearwardly extending scale pan 13, having one end of a pipe 12 attached to the rear end thereof, pipe 12 extending vertically, upwardly therefrom, a rod 10 being horizontally mounted without clearance of any kind through an appropriate opening in the other end of pipe 12, rod 10 carrying a fastening wire 9 for the collection bell jar 8. The total weight of these connecting elements (9,10,12,13) in combination approximately equals the weight of the original scale pan. The scale pan 13 and the pipe 12 can for example be made of aluminum, the rod 10 of brass and the wire 9 of steel, brass or the like.

The weighing results are transmitted to a computer.

In a further aspect of the invention, a device for taking samples of fresh concrete, mortar or the like is disclosed, with a view to determining the air bubble size distribution in said samples by the method of the invention.

Figure 4:
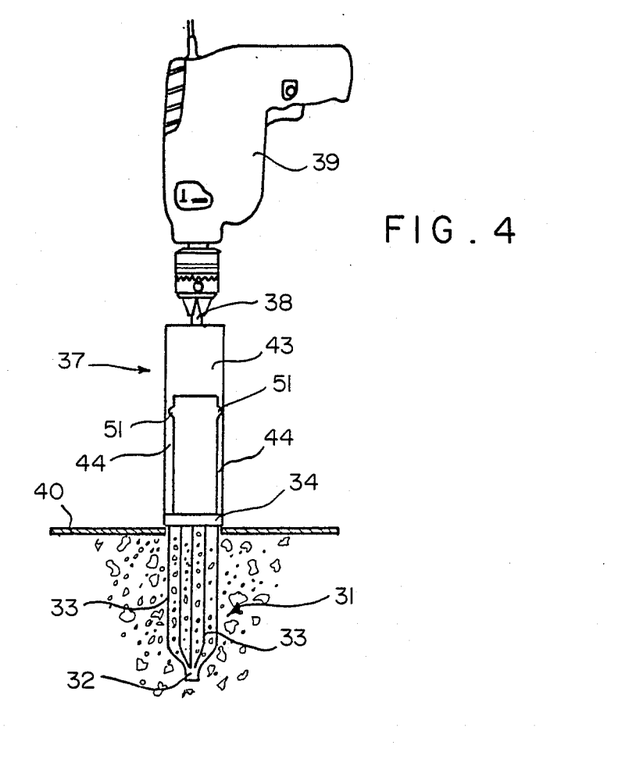
FIG. 4 is an elevational view showing the sample taking device of the invention, comprising an adapter 37 connected with a drill 39, and a sample container 31.
Figure 5:
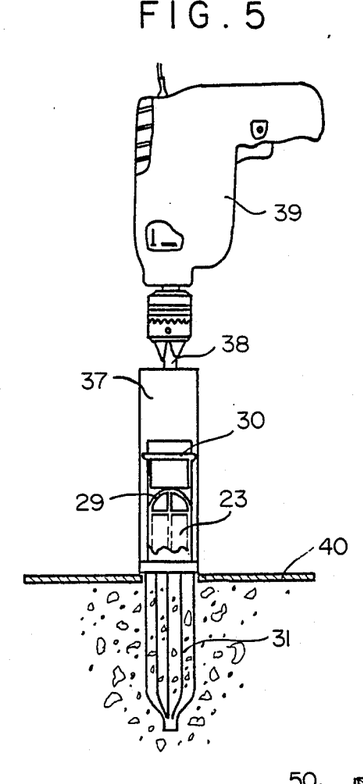
FIG. 5 is a view similar to FIG. 4 principally showing the mounting of a syringe 27 at the adapter 37 being principally shown, FIG. 6 a cross-sectional view of the sample container 31 of the device shown in FIGS. 4 and 5.
Figure 7:
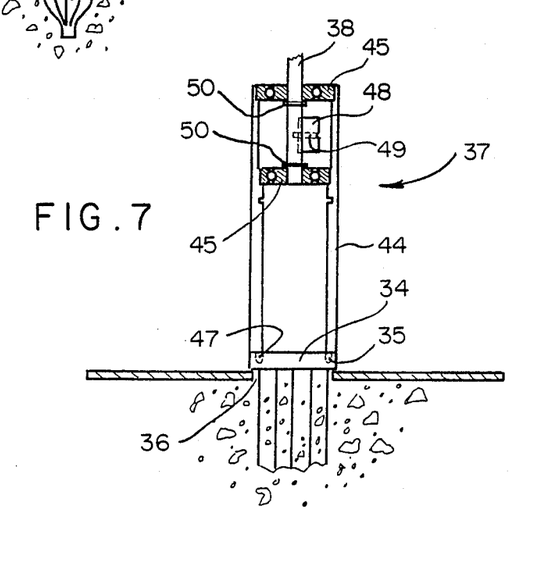
FIG. 7 is a cross-sectional view of the adapter 37 of the device of FIGS. 4 and 5.

The sample taking device comprises a sample container 31 having holes, openings or throughbores therein and an adapter 37 comprising a shaft 38 to be rotated by an electrical motor, preferably a power drill 39, one or more excentrically mounted blocks 48 on shaft 38, ball bearings 45 surrounding shaft 38 and a housing 43 having at least two axially extending legs 44, legs 44 carrying connecting means 47 for engaging the sample container 31.

Having lockingly engaged the sample container 31 and the adapter 37 and having connected the shaft 38 to the power drill 39, shaft 38 by activating the power drill 39 will rotate and, because of the excentrically mounted blocks 48, vibrate, too. The vibrational but not the rotational movement is transferred to the housing 43 and legs 44 via the ball bearings 45, and to the sample container 31, being engaged with the adapter 37. When now slowly lowering this vibrating sample container 31 down into a batch of fresh concrete, the concrete will become somewhat plastic, a floating or flooding of the concrete as a compact mass into the sample container occurs, leaving those coarse aggregates behind that cannot enter the sample container because of their size. Accordingly, a sample of the actual batch of fresh concrete results, on the whole unchanged, apart from the coarse aggregates, being pushed aside, the discriminating size of said coarse aggregates being determined by the size of the openings in the sample container 31.

When performing the method according to the invention, the coarse aggregates are undesired, because of the risk of blocking the sample introducing device 27, the risk of hampering the movement of the magnetic pin 5 and the risk of blocking the proper ascension of the released air bubbles. Using the preferred analytical assembly and the preferred method of the invention, the desired discriminative size of the coarse aggregates is about 6 mm, particles bigger than about 6 mm being wanted to be left behind, any other size, however, possibly being discriminative using other embodiments of the invention.

In the sample container 31, holes of various shapes can be used, for instance circular, rectangular or quadratic holes, as long as the size of the holes corresponds to the desired discriminative size of the coarse aggregates.

The locking or connecting means 47 on adapter 37 for the engagement of corresponding connecting means 35 on said sample container 31 can be elaborated in various ways, for example, the legs 44 of the adapter can be externally threaded and the sample container correspondingly internally threaded or vice-versa, or a number of different catch lock devices can be used. In a preferred embodiment, the connecting means comprise locking hooks 47 on the adapter legs 44 and corresponding recesses 35 in the upper part of the sample container, the engagement and disengagement of which results from slightly pressing the legs 44 together.

Figure 6:
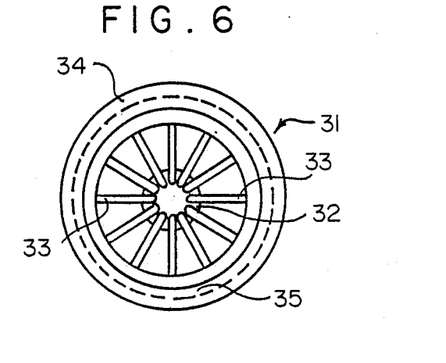

A sample container 31 having a grating of a bird cage resembling type as shown in FIG. 6, i.e. comprising an upper ring 34 and a number of wires 33 attached thereto, the wires 33 being distributed along the circumference of the upper ring 34 and being directed primarily in the direction of the longitudinal axis of the rotating shaft 38, at the bottom part of the sample container 31 further bending inwardly under adjustment to the smaller circumference of a lower ring 32, to which they are attached as in the upper end, is further advantageous, because the distance between neighboring wires gradually increases, when passing from the lower ring 32 to the upper ring 34, for example from about 2 mm to about 7 mm. When using an embodiment of the sample container with circular or quadratic holes of a width of about 6–8 mm instead of the just described embodiment, there is a great risk of the coarse aggregates blocking the holes, the risk being eliminated when using the above mentioned embodiment, comprising a grating. The gradually increasing distance between the wires 33 leads to slowly upwardly moving aggregates of particles of a size bigger than 2 mm, those of a smaller size than 7 mm finally entering the sample container, at a place where the appropriate distance is encountered, the coarsest aggregates being left behind.

The upper and the lower ring 34 and 32, respectively, can be made of any suitable material, for example stainless steel, copper, brass and plastic materials, preferably brass, and the upper ring 34 carries on its inside a recess 35 for connection with hooks 47 on the adapter legs 44. The wires 33 are preferably made of stainless steel, being attached to the rings 32, 34 by hard-soldering (brazing).

In a further preferred embodiment of the sample taking device, the adapter shaft 38 further comprises sealing or locking discs 50, being made of special spring steel and being mounted in corresponding recesses in shaft 38 immediately after and before the upper and lower ball bearing 45, respectively. These serve to secure and stabilize the position of said shaft 38, relative to the housing 43, when for instance utilizing a hammer drill 39.

In another preferred embodiment recesses 51 are made on the inside of the adapter legs 44, for engaging the rear enlargement 30 of the inner piston 29 in the sample syringe 27. The fact is that syringe 27 with advantage can be mounted between the adapter legs 44 before the sample taking procedure, as described below.

In a preferred embodiment, the shaft 38 of the adapter 37 is made of stainless steel, the housing 43 including the legs 44 of stainless steel, copper, brass, aluminium, plastic or the like, preferably aluminum. One excentrical block 48 is preferably attached to the shaft 38 using a fastening screw 49.

The sample taking procedure, when utilizing the device according to the invention, proceeds as follows: The adapter 37 is lockingly combined with the sample container 31, and the sample syringe 27 is positioned between the adapter legs 44, the enlargement 30 in the recesses 51. A supporting plate 40, preferably of impact-proof polycarbonate, having a suitable opening 36 for the grating of the sample container 31, is laid upon the actual batch of fresh concrete. The extending end of the shaft 38 is secured to the rotating and/or hammering power drill 39, which is then turned on, causing the sample container 31 to vibrate. The device as a whole is then slowly lowered down through the opening 36 in the supporting plate 40, until the abutment of the upper ring 34 against this plate 40. After only a few seconds, the sample container 31 is filled up, the outer shield 23 of the syringe 27 is pushed ahead, penetrating the sample volume in the sample container 31 and confining a part of it. Finally, the device as a whole is raised, the elements being separated and properly cleaned, the syringe 27 now carrying a suitable sample 28 of fresh concrete.

The sample is now ready for the determination of the air bubble size distribution by the method according to the invention, said procedure in the following being described in general terms, only the one embodiment of two media being applied, viz. a lower bubble preserving sample suspending medium 16 and an upper medium 17. Of course, according to the invention just one medium or more than two media can be applied, too, anyhow, these procedures are analogous.

The analytical assembly of the invention as shown in FIG. 1 is used. The perforation 4 in the bottom section 1 is closed by the thermo feeler 21 in its housing 22. The magnetic pin 5 is placed upon the heating plate 3 at the bottom of the section 1. A suitable amount of the upper medium 17 having an appropriate temperature is then transferred to the sectionally divided container, any air bubbles on the inside of said container gently being brushed off. Then a suitable amount of the lower medium 16 having an appropriate temperature is pipetted off and carefully transferred to the bottom of the bottom section 1, in order to obtain a distinct layer of separation along the dividing line 18. The lower medium 16 is for practical reasons preferably colored. Finally, the collection bell jar 8 is immersed into the upper medium 17, the internal volume of air being replaced by an equal volume of the medium 17, the air escaping through a tiny hole in the bottom of the bell jar 8, the hole being located very close to the walls, outside the air bubble ascending area, as generally determined by the width of the intermediate section 6. Then the analytical assembly is prepared for the introduction of the sample 28.

While slowly withdrawing the housing 22 with the thermo feeler 21 from the one part of the throughgoing perforation 4, the syringe 27 is correspondingly introduced into that one part, finally reaching the position, as shown in FIG. 3. Now the thermo control unit is activated, ensuring the maintaining of a desired constant temperature during the analyzing procedure, and the sample 28 (typically 20 ml) is introduced by pushing the inner piston 29 forwardly, the empty syringe 27 remaining in the opening. The analyzing procedure starts at time zero, using a stop watch for example, (not shown), with; after the scale 14 set at zero by switching on the agitator 15. After operating for 30 sec., for example, the agitator is automatically switched off, the air bubbles in the sample now being released and ascending through the media 16 and 17.

The resulting velocity of an air bubble rising in a liquid medium is according to an acknowledged fact proportional to the diameter, raised to a power greater than one. The same is true of spherical particles sinking in a fluid under the influence of gravity. For our system, this fact is confirmed: The bigger air bubbles leave the lower medium and ascend more quickly towards the surface of the upper medium than the smaller air bubbles so that the time of passage through a given level in the upper medium 17 of the individual bubbles will reflect the diameter of the air bubble concerned.

In a usual analyzing procedure, the air bubble weight-time-relationship is measured for each sample, the measurement in connection with the size-time-measurement from the calibration procedure, resulting in the desired air bubble size distribution, for example expressed as the weighted specific surface of the air bubble system or in other mathematical terms, (see Example 1 below).

The weighing figure, being read on the digital scale, will start at zero and gradually decrease ($-0{,}27$ g, $-0{,}52$ g, etc.), as time passes. After, for examples 30 min. (depending on the amount of the sample, the elected media, the temperature, the stirring time and the velocity), practically all released air bubbles have been registered, and the analyzing procedure is over.

The analyzing procedure is described above. The analyzing set up should also be calibrated. This calibration, or the relationship between bubble size and time, is established in a separate procedure (see the description below), the calibration being necessary only once for a given system.

When calibrating the assembly, i.e. when establishing the size-time-relationship, the same procedure as just described is used, the collection bell jar 8, however, not being immersed, and no weighing thus resulting. Instead, at appropriate intervals, one half of a conventional frame for a diapositive is immersed into the upper medium 17 catching the air bubbles being present at the level of immersion and, when combining the one half of the diapositive frame with its counterpart, fixing them in a stable condition for at least 30 min., until the analyzing procedure is over. Then the different diapositives, confining the samples being taken at time 15 sec., etc., are examined microscopically, preferably a microphotograph is taken, and the maximum air bubble size is determined for each diapositive, resulting in the desired relationship between size and time, (see Example 1 below).

Figure 8:
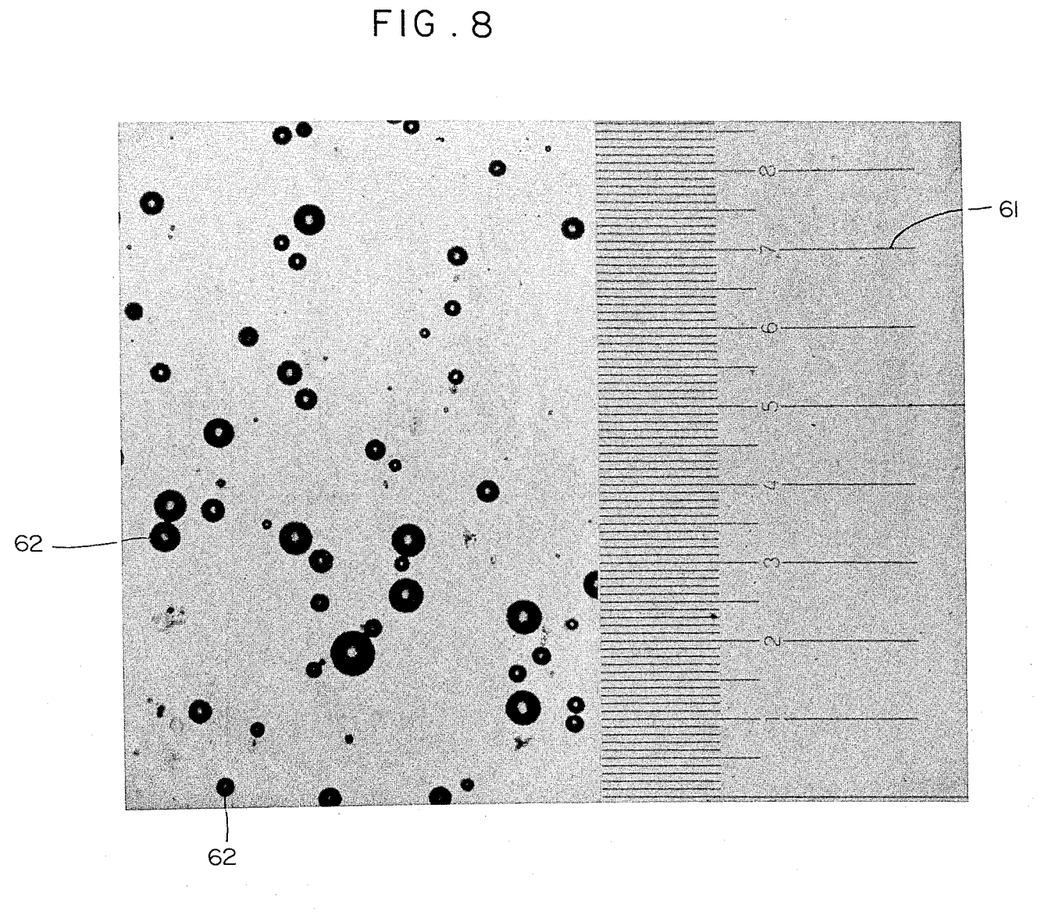
FIG. 8 is a microphotograph of those released airbubbles which are passing a certain level 1 min. after the starting up of the analyzing procedure.
Figure 9:
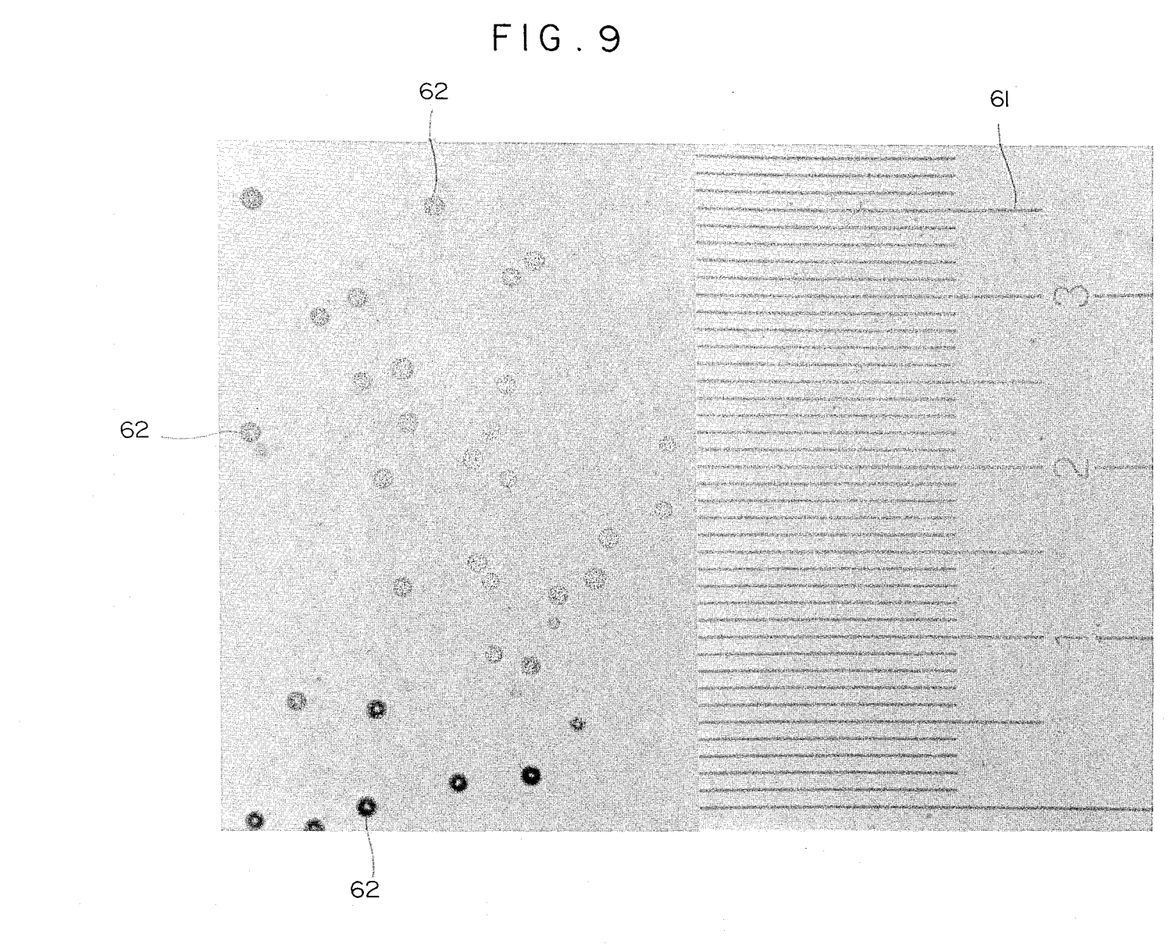
FIG. 9 is a view similar to FIG. 8, but after 9 min.

The microphotographs in FIG. 8 and 9 where taken at time 1 min. and 9 min., respectively. A 0.5 mm scale 61 is shown, enabling the determination of the size of the air bubbles 62. In FIG. 8, the maximum air bubble diameter appears to be about 0.5 mm, and in FIG. 9 about 0.1 mm, clearly demonstrating the fact that the bigger air bubbles are ascending more quickly.

EXAMPLES

EXAMPLE 1; UPPER MEDIUM WATER, LOWER MEDIUM GLYCEROL

This Example deals with the analysis of two samples from two different batches of fresh concrete taken using the sample taking device of the invention. In the following these two samples are are referred to as sample F 21 and sample E 3; A volume of 1500 ml of demineralized water as the upper medium was transferred to the sectionally divided container, and air bubbles on the inside, if any, were carefully removed, using for example a brush. Then 200 ml of 85% glycerol (from Bie & Berntsen, Denmark, Art. No. BBB 16030) as the lower sample suspending bubble preserving medium containing a few drops of methylene blue was transferred to the bottom section, thus establishing in the container a two layer system consisting of a lower glycerol layer and an upper water layer. The collection bell jar was immersed into the upper medium, any air bubbles on the inside being carefully removed, and the electrical heating device was switched on and the obtainment of the desired temperature (23° C.) is awaited. Then the 20 ml sample of fresh concrete from the syringe was introduced into the perforation in the bottom section, and the weighing unit was set to zero. The magnetic agitator was turned on and operated for 30 sec. and was then stopped. The time was set to zero, and the automatic registration of the buoyancy of the immersed collection bell jar as a function of proceeded for 30 min.

The following results are obtained:

| Sample F 21 (vol. 20 cm³): | |
|---|---|
| Analysis time | Buoyancy (g × 10⁻³) |
| 0 sec. | 0 |
| 15 sec. | 40 |
| 30 sec. | 770 |
| 45 sec. | 920 |
| 60 sec. | 970 |
| 90 sec. | 1060 |
| 120 sec. | 1110 |
| 3 min. | 1160 |
| 4 min. | 1180 |
| 5 min. | 1200 |
| 7 min. | 1220 |
| 10 min. | 1240 |
| 15 min. | 1270 |
| 20 min. | 1290 |
| 25 min. | 1300 |

| Analysis time interval sec. | Buoyancy gained in interval g × 10⁻³ | Volume of average bubble mm³ | Equivalent Nos. of bubbles |
|---|---|---|---|
| 0–15 | not incl. | — | — |
| 15–60 | 930 | 2.30 | 404 |
| 60–120 | 140 | 0.055 | 2,545 |
| 120–180 | 50 | 0.021 | 2,381 |
| 180–240 | 20 | 0.0115 | 1,739 |
| 240–300 | 20 | 0.0070 | 2,857 |
| 300–420 | 20 | 0.0032 | 6,250 |
| 420–600 | 20 | 0.0016 | 12,500 |
| 600–900 | 20 | 0.00125 | 16,000 |
| 900–1500 | 30 | 0.0010 | 30,000 |

Total buoyancy 1,250 mm³ (g × 10⁻³)
Total number of air-voids in sample 74,676

The average diameter (volume) of air-voids recorded in the buoyancy figure for the analysis interval has been determined in a previous calibration procedure.

Average volume of air-voids: 1 mm³ corresponds to a buoyancy of $1g \times 10^{-3}$.

$$\frac{\text{Buoyancy}}{\text{Nos. of air-voids}} = \frac{1250}{74,676} = 0.0167 \text{ mm}^3 = \frac{4}{3} \cdot \pi \cdot r^3$$

$$r^3 = 0.004, r = 0.16 \text{ mm}$$

Specific surface, alpha = 18.8 mm⁻¹
Percentage of mortar in concrete (estimated from composition): 44%.
Air-void content in concrete:

$$\frac{1.27}{20} \times 44 = 2.8\%$$

According to the known art (ASTM C. 457) the following result are obtained by analysing the hardened concrete, corresponding to the sample F. 21:
Air content (air bubble diameter < 2 mm): 2,8%, by volume of concrete
Spec. surface (air bubble diameter < 2 mm): 17,9 mm⁻¹
The correspondence is seen to be very good.

| Sample E 3 (vol. 20 cm⁻³): | |
|---|---|
| Analysis time | Buoyancy (g × 10⁻³) |
| 0 sec. | 0 |
| 15 sec. | 250 |
| 30 sec. | 340 |
| 45 sec. | 410 |
| 60 sec. | 470 |
| 90 sec. | 580 |
| 120 sec. | 700 |
| 3 min. | 910 |
| 4 min. | 1100 |
| 5 min. | 1270 |
| 7 min. | 1540 |
| 10 min. | 1990 |
| 15 min. | 2250 |
| 20 min. | 2420 |
| 25 min. | 2550 |
| 30 min. | 2560 |

| Analysis time interval sec. | Buoyancy gained in interval g × 10⁻³ | Volume of average bubble mm³ | Equivalent Nos. of bubbles |
|---|---|---|---|
| 0–15 | not incl. | — | — |
| 25–60 | 200 | 2,30 | 96 |
| 60–120 | 230 | 0,055 | 4,182 |
| 120–180 | 210 | 0,021 | 10,000 |
| 180–240 | 190 | 0,0115 | 16,522 |
| 240–300 | 170 | 0,0070 | 24,286 |
| 300–420 | 270 | 0,0032 | 84,375 |
| 420–600 | 450 | 0,0016 | 281,250 |
| 600–900 | 260 | 0,00125 | 208,000 |
| 900–1500 | 300 | 0,0010 | 300,000 |

Total buoyancy 2,300 mm³ (g × 10⁻³)
Total number of air-voids 928,711

$$\frac{2{,}300}{928{,}711} = 0.02476 \left( = \frac{4}{3} \cdot \pi \cdot r^3 \right)$$

$$r = 0.084 \text{ mm}$$

Specific surface, alpha=35.8 mm$^{-1}$
Percentage of mortar in concrete: 48.7%
Air-void content in concrete:

$$\frac{2.30}{20} \times 48.7 = 5.6\%$$

The hardened concrete was subjected to analysis according to ASTM C 457:
Air content (diameter<2 mm): 5.5% by volume of concrete
Spec. surface (diameter<2 mm): 35.8 mm$^{-1}$ Again the results obtained by the two methods are very much alike.

Conclusion:

The air bubble system of the sample E 3 is satisfactory, yielding a sufficient protection of the concrete against frost damages, whereas the sample F. 21 must be rejected.

By using the method according to the invention the whole batch of fresh concrete corresponding to the sample F. 21 could be rejected before casting it, this evidently being a great advantage.

EXAMPLE 2; UPPER MEDIUM WATER, LOWER MEDIUM ETHYLENE GLYCOL

The air bubble size distribution in a sample of fresh concrete was determined using the procedure of Example 1, apart from the lower bubble preserving medium being ethylene glycol (extra pure, >99%, Merch. Art. 949) instead of glycol (extra pure, >99%, Merch. Art. 949) instead of glycerol.

EXAMPLE 3; UPPER MEDIUM WATER, LOWER MEDIUM PROPYLENE GLYCOL

As outlined in Example 1 and 2 above, the air bubble size distribution in a sample of fresh concrete was measured using propylene glycol (pure, from Struers, Denmark, Art. No. 311408-02) as the lower sample suspending medium.

EXAMPLE 4; UPPER MEDIUM WATER, LOWER MEDIUM SUCROSE

A 60% (w/v) solution of sucrose (extra pure, from Merch, Art. No. 7653) in water was manufactured by slowly adding 600 g sucrose to 1000 ml water under continuous stirring. This solution was used in the method according to the invention as the lower bubble preserving sample suspending medium.

I claim:

1. A method of determining the air bubble size distribution in fresh mortar, concrete and the like, comprising:
   taking a suitable sample from a batch of fresh concrete;
   forcing air bubbles out of said sample;
   passing said air bubbles into a bubble preserving sample suspending medium at a constant temperature;
   registering the amount of said air bubbles over a period of time;
   measuring the size and number of said air bubbles at appropriate intervals and establishing an empirical relationship; and
   determining the actual air bubble size distribution by utilizing said relationship with said registration.

2. The method as claimed in claim 1, wherein:
   said bubble preserving sample suspending medium comprises a lower medium of at least one liquid selected from the group consisting of glycerol, a glycol, an alcohol, mixtures of alcohol with water, a solution of at least one salt, a carbohydrate solution, a suitable dye, and mixtures thereof; and
   said bubble preserving sample suspending medium further comprises an upper medium superposed over said lower medium and comprising at least one liquid selected from the group consisting of water, salt solutions, carbohydrate solutions, detergent solutions, and mixtures thereof.

3. The method as claimed in claim 2 wherein said media are selected from the group consisting of
   glycerol as the lower bubble preserving sample suspending medium, being superposed by water as the upper medium at a temperature from approximately 18°–25° C.;
   ethylene glycol as the lower bubble preserving sample suspending medium, being superposed by water as the upper medium;
   a propylene glycol as the lower bubble preserving sample suspending medium, being superposed by water as the upper medium; and
   a 60% (w/v) solution of sucrose in water as the lower bubble preserving sample suspending medium, being superposed by water, as the upper medium.

4. The method as claimed in claim 3 wherein:
   said air bubbles are forced from said sample of fresh concrete by agitating said sample; and
   the air bubble amount is registered automatically as a function of time using a volumetric scale reading.

5. The method as claimed in claim 4 wherein said air bubbles are released from said sample by agitation using a magnetic stirrer and the air bubble weight is registered continuously as a function of time by measuring the increase of the buoyancy of a collection bell jar immersed in said upper medium.

6. The method as claimed in claim 3 wherein:
   said air bubbles are forced from said sample of fresh concrete by agitating said sample; and
   the air bubble amount is registered automatically as a function of time by immersing a collection bell jar in said upper medium and measuring the increase of the buoyancy of said immersed bell jar.

7. The method as claimed in claim 6 wherein the air bubble size-time-relationship is established by taking representative samples of the upper superposed medium comprising the released air bubbles at appropriate time intervals, preserving said samples in a fixed state with no change in the air bubble size distribution occurring, and determining the maximum, minimum or mean air bubble size in each of said samples microscopically.

8. The method as claimed in claim 7 wherein said samples of the upper superposed medium are taken using one half of an immersed frame for a diapositive, and said samples are fixed by lockingly combining said one half of the frame with the counterpart of said frame.

9. An analytical assembly for determining the air bubble size distribution in fresh mortar and concrete by using a method in which the air bubbles are forced out of a sample of concrete and into a bubble preserving sample suspending medium at a constant temperature, the amount and the size of said released air bubbles being registered as a function of time, the assembly comprising:

a weighing scale having a scale pan;
a magnetic agitator means for agitating the sample;
electrical heater means for heating said sample;
a temperature control unit connected with said electrical heater means;
a container for the sample and bubble preserving sample suspending medium comprising a bottom section, an intermediate section of increased internal width relative to the bottom section and an upper section of still further increased internal width; and
a collection bell jar immersed in the bubble preserving sample suspending medium for collecting air bubbles therein and mechanically connected with said scale pan for weighing said bell jar.

10. The analytical assembly as claimed in claim 9 wherein said sections of said container are made of materials selected from the group consisting of stainless steel, glass, plastic material, and polymethylmethacrylat (PMMA, Plexiglas (R) ).

11. The analytical assembly as claimed in claim 10 wherein:

a housing is provided for the scale and the agitator, said bottom section is fastened in said housing and contains said electrical heater;
at least one perforation is provided through said bottom section;
a plurality of packing rings are provided in said perforation; and
a thermometer and a sample introducing syringe are tightly engageable in said packing rings.

12. The analytical assembly as claimed in claim 11 wherein said container sections. have a circular cross section.

13. The analytical assembly as claimed in claim 12 wherein:

said bottom, intermediate and upper sections have heights with a ratio of approximately 1:4:1, respectively and diameters with a ratio of approximately 5:6:8, respectively.

14. The analytical assembly as claimed in claim 13 wherein:

said scale pan has a rear portion;
a pipe is attached to said rear portion and extends vertically therefrom;
a rod extends horizontally through an opening in said pipe; and
a fastening wire is connected to said rod and to said collection bell jar for supporting said bell jar from said rod.

* * * * *